United States Patent
Caceres et al.

(12) 
(10) Patent No.: US 7,048,976 B2
(45) Date of Patent: May 23, 2006

(54) COOLING ARTICLE INVOLVING EVAPORATION OF WATER FROM A POLYMER ABSORBENT

(75) Inventors: Patrick Caceres, Lyons (FR); Frank Caceres, Lyons (FR)

(73) Assignee: Cryomed France, Allauch (FR)

( * ) Notice: Subject to any disclaimer, the term of this patent is extended or adjusted under 35 U.S.C. 154(b) by 267 days.

(21) Appl. No.: 10/026,629

(22) Filed: Dec. 27, 2001

(65) Prior Publication Data

US 2002/0076533 A1 Jun. 20, 2002

Related U.S. Application Data

(63) Continuation-in-part of application No. 09/227,889, filed on Jan. 11, 1999.

(30) Foreign Application Priority Data

Apr. 3, 1997 (FR) .................................. 97 01972

(51) Int. Cl.
   *B29D 23/00* (2006.01)
(52) U.S. Cl. ..................... 428/34.7; 428/343; 428/71; 428/402; 428/407; 128/101.1; 128/112.1; 126/204; 165/46; 602/45; 602/46; 602/56; 602/58; 602/76; 607/96; 607/108; 607/109; 607/110; 607/111; 607/112; 607/113; 607/114; 604/385.19; 604/366; 604/369; 604/358; 604/370; 604/290; 604/543; 604/317
(58) Field of Classification Search ................. 607/96, 607/108–112, 114; 602/45, 46, 56, 58, 76; 424/443–448; 165/46; 126/204; 128/89, 128/101.1, 112.1; 428/402, 407, 71, 34.3, 428/34.7; 604/290, 543, 317
See application file for complete search history.

(56) References Cited

U.S. PATENT DOCUMENTS

| | | | | |
|---|---|---|---|---|
| 4,297,410 A | | 10/1981 | Tsuchiya et al. | |
| 4,897,297 A | * | 1/1990 | Zafiroglu | 428/102 |
| 5,060,642 A | * | 10/1991 | Gilman | 602/56 |
| 5,129,391 A | * | 7/1992 | Brodsky et al. | 607/110 |
| 5,147,646 A | * | 9/1992 | Graham | 424/424 |
| 5,447,531 A | * | 9/1995 | Wood | 607/108 |
| 5,486,206 A | * | 1/1996 | Avery | 607/104 |
| 5,597,577 A | | 1/1997 | Mathewson | |
| 5,597,873 A | | 1/1997 | Chambers et al. | |
| 5,606,746 A | | 3/1997 | Shelton et al. | |
| 5,669,894 A | * | 9/1997 | Goldman et al. | 604/368 |
| 5,879,378 A | * | 3/1999 | Usui | 607/96 |
| 6,075,177 A | * | 6/2000 | Bahia et al. | 602/43 |
| 6,152,952 A | * | 11/2000 | Owens | 607/108 |
| 6,169,223 B1 | * | 1/2001 | Mahr et al. | 602/56 |
| 6,270,873 B1 | * | 8/2001 | Darnett | 428/76 |
| 6,329,565 B1 | * | 12/2001 | Dutkiewicz et al. | 604/378 |
| 2003/0109910 A1 | * | 6/2003 | Lachenbruch et al. | 607/108 |

FOREIGN PATENT DOCUMENTS

| | | |
|---|---|---|
| CA | A-2135966 | 5/1996 |
| DE | A-29519564 | 3/1996 |
| EP | 0 789 048 A1 | 8/1997 |
| FR | A-2719892 | 11/1995 |
| JP | A-8-71099 | 3/1996 |
| WO | WO 02063984 A2 * | 8/2002 |

* cited by examiner

*Primary Examiner*—Rena Dye
*Assistant Examiner*—Tamra L. Dicus
(74) *Attorney, Agent, or Firm*—Oliff & Berridge, PLC

(57) ABSTRACT

The invention relates to a cooling article comprising a polymer absorbent enclosed within a bag delimited by a collapsible envelope having non-watertight walls, wherein said polymer absorbent is under the form of particles each of which comprises a core of less cross-linked polymer sequences more active in retaining absorbed water and a shell of more cross-linked polymer sequences apt to retard diffusion of water from a particle to another during desorption of absorbed water.

23 Claims, No Drawings

COOLING ARTICLE INVOLVING EVAPORATION OF WATER FROM A POLYMER ABSORBENT

This is a Continuation-in-Part of application Ser. No. 09/227,889 filed Jan. 11, 1999. The entire disclosure of the prior application is hereby incorporated by reference herein in its entirety.

FIELD OF THE INVENTION

The present invention relates to such cooling devices as are useful for relieving pain from a sore or painful part of an individual's body. Pain relief is here considered as including reduction to any extent as well as complete alleviation of pain, for at least some amount of time. The main object of the invention is to provide such an article that will exhibit a high and long-lasting cooling capability when applied externally on said sore part and will be non toxic and easy to use.

However, the invention is not restricted to that field of application of the articles it provides and it extends as well to a great number of other applications where it is desired to bring or maintain an object to a temperature lower than that of the ambiance where it stands. More specifically the invention relates to such cooling articles the operation of which involves evaporation of water.

BACKGROUND OF THE INVENTION

Cryogenics has been used for a long time as a means to relieve pain, and its beneficial effects on health and comfort are well-known.

The precursor to all existing cooling articles for pain relief is the ice bag, which however presents a major drawback, due to the fact that it offers a non-homogeneous cooling surface. In order to achieve some flexibility and adapt thereby to the form of the member or part to be cooled, the ice-bag has to be filled with ground ice, which requires that the bag can be opened. Although this allows a closer contact over the whole sore part than full solid ice in the ice-bag, ground ice, because it is made of small pieces, involves for the bag in which it is enclosed a non-homogeneous cooling contact with the surface to be cooled. Furthermore, as soon as the ice melts, the liquid water produced concentrates into the lower part of the bag, thus increasing the lack of homogeneity of the cooling effect.

During the last decades, new cooling articles have been s developed that show good thermal properties and better stability in their close contact with the surface to be cooled. In those commercially available a heat transfer medium made of an aqueous gel of propylene glycol and/or methylcellulose is used in the frozen state instead of ice. The gel is enclosed in an impervious film of organic material. Such is the case for instance for the cryogenic gel commercially known as a blue gel or the device known under the trademark Cold Hot 3M.

It has further been proposed to produce a higher cooling effect by permitting evaporation of water out of a highly absorbent medium swollen with water through an envelope made of a polyester fabric or some other permeable material. Examples for such devices are disclosed in Canadian patent application 2 135 966, the content of which is herein incorporated by reference. It can be understood therefrom that the medium enclosed in the non-waterproof envelope is in the form of a powder of polymer particles when dry, and it does not operate merely as a heat transfer medium. The enclosure is permeable to moisture as well as to water, and the article continues to produce a cooling refreshing effect during desorption of the water previously absorbed that escapes from the particles.

However, it is still desirable to enhance the properties of such articles and achieve a longer cooling effect. An article with a regularly homogeneous cooling effect which lasts over time can be useful in various industrial applications, for instance to preserve freshness of food or medecines, but proves especially useful in therapeutic applications, for removing extra heat from a member or part of the body to be treated.

SUMMARY OF THE INVENTION

Thence, an object of the invention is to provide an article showing cooling properties that are highly improved compared to the prior art. The article of the invention is made of particles of a highly absorbent polymer enclosed within a bag delimited by an advantageously collapsible envelope having non-watertight walls. It differs from those previously known by the fact that water, by evaporating from the article after it has been immersed in water, will provide a long-lasting cooling effect with slow heat uptake.

A further object of the invention is to ensure that although steam can easily escape out of a bag delimited by the envelope through a wall of the bag constituting an outer face of the envelope, an opposed inner face of the envelope supplies a so-called dry cold when applied onto a part to be cooled. As a consequence the wearer will never have the impression that the surface of the bag has become wet and heat transfer at the contact with the skin will not be disturbed.

Still another object of the invention is to ensure that the thermal shock corresponding to the temperature difference at the interface between the article and the part to cool is homogeneous all over that part and that it remains constant along time.

In connection with that purpose, the invention provides a cooling article involving evaporation of absorbed water from an absorbent polymer wherein said polymer is enclosed in a bag delimited by an envelope comprising a heat-conductive inner wall for contact with a part to be cooled and an opposite outer wall permeable to moisture escaping from the polymer medium during desorption.

Other objects and advantages of the invention will appear from the description below of preferred embodiments of the article according to the invention, They include the fact that in preferred embodiments all matters and materials in the article should be non-toxic for medical external uses and should satisfy to all security requirements in that field.

According to a main feature of the invention, the absorbing/desorbing medium is made of polymer particles showing a shell-core structure, i.e. that are individually composed of a core with relatively flexible or elastic sequences and a shell of relatively more rigid polymer sequences. The difference in rigidity, or stiffness, can be achieved at best by additional cross-linking of the polymer in an outer layer of each particle compared to an inner layer forming the core. In such cases, the outer shell in each particle shows the structure of a tridimensional reticulate net, or web, that does not preclude inflation of the particle when absorbing water up to the swollen state, but facilitates flowability and sliding of the particles on one another with little friction, while during desorption it avoids close wet contact between the soaked cores and introduces thereby some delay on the diffusion of water from each particle to the next ones.

Thus, a cooling article according to the invention comprises a polymer absorbent enclosed within a bag delimited by a collapsible envelope having non-watertight walls, and said polymer absorbent is under the form of particles each of which comprises a core of less cross-linked polymer sequences more active in retaining absorbed water and a shell of more cross-linked polymer sequences apt to retard diffusion of moisture from a particle to another during desorption of absorbed water.

The envelope according to the invention is advantageously flexible and collapsible. As a result, the thickness of the article, very low when the polymer particles are in the dry state, increases when the particles swell. Then, during water desorption, the size of the particles decreases, water escapes from the article and owing to its flexibility, the envelope collapses, meaning that its inner and outer walls come close together. In consequence there is little, or no, air entry in the envelope. This is of a particular importance, because some air present in the envelope would disturb heat transfers between the sore part of the body and the water absorbed in the particles, and thus would decrease the efficiency of the long-lasting cooling effect of the article.

Furthermore, the shape of the inner wall of the flexible envelope according to the invention is easily adapted to that of the part of the body to which the article is applied, which provides a better pain relief on the entire painful surface.

In the preferred embodiments the walls of the envelope are made of textile.

A method for relieving pain from a sore part of an Individual's body with a cooling article according to the invention comprises wetting said polymer particles with water through said envelope during a sufficient time to swell them into a gel mass filling up said bag, and applying said article on said sore part of the body, thereby maintaining an inner wall in close contact thereon while allowing water vapour desorbed from said particles to escape through an outer wall of said envelope.

According to a secondary feature of the invention, the amount of polymer particles enclosed in the bag is in excess compared to that which would just be required to fill up the bag when they are in the full swollen state. Due to such an excess in connection with the specific structure of the particles, it has been observed that during absorption of water there occurs some expansion of the mass, with light particles not yet completely swollen with water that have a tendency to be expelled from the center where completely swollen particles concentrate into a gel. Thence at the end of the absorption process there remains, close to the walls of the bag, a layer of particles that would still be able to absorb some water. Those particles are useful to absorb any trace of water, moisture or sweat penetrating into the bag through the envelope, which maintains the latter dry. There is thereby provided a better feeling of comfort for the user, and a better heat transfer across the inner wall of the envelope is achieved. Moreover this layer of not fully swollen particles constitutes an additional barrier to water outlet, which increases the thermal inertia of the article according to the invention.

According to a further important feature of the invention, the fabric for the envelope is composed so as to be resistant to the pressure of the swollen gel mass, during and after water absorption. Preferably, it is also composed so as not to be water-absorbent, so that it does not let water diffuse easily through it out of the gel mass. Fibers showing hydrophobic or water-repellent behaviour can advantageously be used therefore. However, for most applications, and especially for the application as a refreshing bandage in medical uses, it has proven specially suitable to use a partly hydrophilous and partly hydrophobic fabric. In preferred specific embodiments of the invention, a convenient fabric is made of natural and/or semi-synthetic fibers such as cotton and/or cellulosic fibers.

COMPLETE DESCRIPTION OF THE INVENTION

Cooling articles according to the invention can be manufactured so as to show a great variety of shapes adapted to be applied onto different parts of the human body to be treated. Convenient shapes are described in Canadian patent 2 136 966 already referred to. However each bag for containing a dose of the polymer medium is preferably of elongated shape with a section having a diameter from 1 to 5 centimeters, preferably less than 3 centimeters, and the whole article may comprise two or more bags, such as can be separated by sewing together two opposite walls of a single envelope Furthermore, whereas that prior art reference provides for using the absorption/desorption process, it is directed to the selection of polymer particles out of potassium polyacrylate that will promote a specific physicochemical effect. The invention avoids the drawbacks of that kind of polymers, which exhibit relatively high cutaneous toxicity, so that their application in articles which have to be applied on the human skin cannot be contemplated. For that purpose, the particles in the absorbent medium used according to the invention have preferably a sodium polyacrylate polymer base.

Other so-called superabsorbent polymers, having high fluid absorption properties, have been described in the literature, but solely for the manufacture of disposable moisture absorbent articles, such as diapers. Thus, U.S. Pat. No. 5,597,873 provides an extensive review of the prior art concerning such superabsorbent polymers. All information disclosed therein is hereby incorporated by reference. The main interest of that reference here is that it discloses superabsorbent polymers that show a shell-core structure as required by the invention. That structure is obtained by submitting a lightly cross-linked base polymer resulting from the polymerization of acrylic monomers to a surface cross-linking process in the presence of an appropriate cross-linking agent. The resulting polymers exhibit improved absorption properties, leading to improved dryness and reduced leakage when used to make disposable diapers.

Preferred polymer particles for use in the articles according to the invention include those described in European Patent Application EP 0,789,048, because they possess a similar shell-core structure and exhibit such properties as good saline water absorptivity, high porosity and high modulus of elasticity. The teachings of this patent are herein incorporated by reference.

It should be noted that both above references refer to the manufacture of diapers only. Thence the polymer particles they describe are used as disclosed in U.S. Pat. No. 4,297,410, wherein particles of a hydrophilous polymer with high absorption properties are incorporated into a felt of non-woven thermoplastic fibers and bound therein by melting. On the opposite, the polymer particles in the article of the invention are separate and not bound together, at least when they are in the dry state, so that they are free to move in the whole volume of the bag where they are enclosed. And surprisingly, it has been discovered that thereby the invention takes benefit of specific properties of the shell-core structure that were unknown previously and lead to unpredictable results. It seems that the highly cross-linked outer layer of each particle forms an expandable lattice that facilitates motion of the particles within the bag, avoids that the swollen particles form a solid hard gel mass, does not hinder the passage of evaporated water from the core, and nevertheless does not permit liquid water to circulate easily through it and thereby diffuse from the core of a particle to a next one.

Furthermore, in connection with the way the polymer particles operate, the invention provides for making use of heat-conductive fabrics for the bag envelope, especially for its inner wall, and for having an outer wall of the envelope made of a rather hydrophilous fabric, at least such that it is permeable to moisture and lets the evaporated water dragged throughout the thickness of the bag escape out of it, whereas in diapers, the outer layer, i.e. the one that is not in contact with the body, must be water-proof in order to avoid leaks.

According to a further advantage of the invention, the shell-core structure increases the mechanical resistance of the individual particle. Rather, one can suppose here that the rigid sequences in the outer highly cross-linked layer explain why the cooling articles of the invention can support a high number of absorption/desorption cycles. The same cooling unit can thence be reused many times with the same efficiency, while each time recovering its properties towards absorption and desorption (especially high thermal inertia and long-lasting cooling effect) after it has been stored in the dry state where the polymer powder is dehydrated.

EXAMPLES OF SPECIFIC EMBODIMENTS

The invention is thereafter described in more detailed examples considering the production of cooling articles intended for use to relieve pain from a sore part of the body by desorption of particles of superabsorbent polymer enclosed in a textile bag.

The particles of superabsorbent polymer are chosen to be non-toxic. In a preferred embodiment, the particles used are made of crosslinked sodium polyacrylate. A maximum level of stability of the polymer is thereby obtained without any toxicological effects.

The polymer particles also have good water absorption/desorption properties. In accordance with the invention, the polymer particles have a shell-core structure, meaning that they possess a flexible part, the core, inside a stiff part, the shell. This is achieved by crosslinking the polymer more on the surface than in the core. Despite its stiffness, the shell part is dilatable, which allows the particles to absorb water and swell into a gel mass. As an example, the volume of the particles can thereby increase up to 60 times their initial volume. The polymer particles thereby obtained show improved absorption/desorption properties compared with homogeneously crosslinked polymers. This is supposed to be at least in part because they are less deformable in the swollen state than in the case of a homogeneous crosslinking.

After having swollen into a gel, the polymer particles according to the invention present very low liquid water desorption properties. Because of their shell-core structure, their external stiffness constitutes a barrier to water oulet. However, if sufficient heat is absorbed by the gel, water can evaporate and is desorbed in the vapour state. After complete desorption, the polymer particles resume their initial dry powder state.

The properties of the particles of superabsorbent polymers according to the invention, and more particularly their porosity and their modulus of elasticity, are not affected by deformation under load, nor by reiterated water absorption/desorption cycles. A gel with intact properties can be regenerated by water absorption after the particles have resumed their initial state, or at any time during the water desorption step. In a preferred embodiment, the setting of the gel can be reproduced 8 to 10 times. As regards the gel formed, this will remain homogeneous.

The polymer particles used are produced according to European Patent application EP 0,789,048, by surface crosslinking a polyacrylic polymer obtained by inverse suspension polymerization of a monomer followed by agglomeration of the individual particles. The precursor monomer can be acrylic acid or methacrylic acid, or preferably a salt thereof, more specifically the sodium salt, but other hydrophilous monomers can also be used.

The amount of particles used, which varies depending on the dimensions of the article, is poured, using a metering device, into a textile bag which may be closed for example by stitching, sewing, or melt bonding. According to the invention, the amount of particles enclosed is selected so that once completely swollen in their gel state, they fill in the entire bag volume.

The bag is delimited by a flexible textile envelope providing a tubular space one to three centimeters wide. At least the fabric for the inner face of the envelope, the one that comes in contact with the body, is selected for showing good heat conductivity properties. The outer face should essentially be permeable to vapour. In a preferred embodiment, the envelope is made of a single fabric, which is permeable to water and water-repellent and which is preferably a cotton or cotton-vicose woven textile fabric. As an example a cotton fabric is used that has not been treated with dye fixers, so as not to retain water.

As used for relieving pain according to the invention, the article shows great initial and long-lasting cooling properties. The different steps of the method will now be explained, together with their supposed mechanisms.

The particles of superabsorbent polymer are wetted by immersion of the article into cold water. Each polymer particle, upon contact with water, absorbs water, starting from its core, so that it swells and forms with the others a gel mass which occupies the entire bag volume. The article is then preferably cooled down in a freezer for better effect. Due to the structure of the polymer particles, it retains a suitable flexibility.

When applying the article on the sore part of the body for which it has been intended, the front face of the envelope comes in close contact with the body. The high difference in temperature between the article and the body and the heat conductibility of the envelope create a thermal shock, with quick heat transfer from the hot body to the cold article, and the user gets a strong immediate feeling of coolness.

At first, the cooling effect and thermal shock may priority be due to the cold temperature of the whole frozen article. But then the heat extracted from the body and slowly transfered accross the article comes to the water trapped in the polymer particles which absorbs it without a temperature increase by changing from the liquid state to the vapour state. The polymer particles architecture provides a barrier to the circulation of water, and their outer shell layer opposes resistance to heat transfer, since the water trapped in the core of each particle must substantially be in the vapour phase before it can escape from it. This results in high thermal inertia and low heat losses.

While water evaporates, the production of steam can slowly progress through the article thickness and reach the external face of the envelope which is permeable to vapour, so that it escapes from the article. Evaporation thence provides an insulating effect due to the absorption of heat. A strong and long-lasting cooling effect is obtained owing to the great quantity of water contained by the polymer particles.

Thus, as long as some water remains in the particles, and up to several days, the article retains its effect of coolness. If not applied to the body, the evaporation process is slow. In order to recover its cooling effect, the article has to be applied on the body. A few days after wetting and cooling, the initial thermal shock does not take place anymore, but owing to the difference of temperature between the body and the article, some heat is transfered and water evaporates, leading to the recovery of the cooling effect.

When all the water has evaporated out of the article, the particles resume their initial state and they gather to an end of the tubular bag as a dry powder. Owing to their good resistance to deformation under load, their initial properties are retained. All that is then required is to immerse the article in water again in order to recover the retention and coolness effect. The swollen article can optionally be kept in a freezer until next use.

As an example of use concerning a specific embodiment of the invention, after the article has been immersed in water at 10° C., for a setting time of the gel of approximately 90 seconds, it shows a heat uptake of between 0.30° C./min. and 0.9° C./min., and more specifically between 0.35° C./min. and 0.7° C./min, with an average value of not more than approximately 0.4° C./min.

The superabsorbent polymer particles for use according to the invention are advantageously in the form of round balls. This makes it possible to trap water not only in the particles but also between these particles, the amount of water trapped between the s particles, known as "interstitial water", being greater in the case of ball-shaped particles than crystal-shaped particles. For the same cross-linking average rate, this leads to a higher absorptivity and therefore, as a result of the larger quantity of water stored, to greater thermal inertia. The ball shape also allows avoiding lacerations or injuries through the textile article, unlike other polymer particles the shape of which is not round and smooth but angular, with sharp edges or in the form of crystals.

Besides, the article of the invention ensures pain relief most efficiently from the largest surface of the sore part. For that purpose, the invention provides for different forms of the article and takes benefit of the properties of the particles of absorbent polymer used such as defined above, especially their ability to flow.

On the one hand, the polymer particles, owing to their round shape and to their shell of rigid polymer sequences, present a high mobility. Consequently, while they are swelling, they are easily distributed homogeneously and move to occupy the entire bag volume, all along its length.

On the other hand, the form of the article according to the invention, which may comprise one or more bags, is designed so as to follow the shape of the part of the body on which it is intended to be applied. The article possesses a part that allows a close contact of the bag(s) containing the polymer particles with the body, such as an elastic band. The polymer particles are enclosed into one or several bags delimited by the envelope. The number and the form of the bags are adapted according to the part of the body that must be treated. They are chosen so as get the best between flexibility and contact surface. A high number of bags enhances flexibility, whereas it decreases the contact surface. In most cases, the bags are advantageously of an elongated tubular form and are assembled along their length.

According to the invention, a so-called dry coolness is achieved. The particles of superabsorbent polymer are enclosed in the bags in such a way that after wetting, the envelope remains dry. The fabric is not absorbent for water. As a consequence, the bag formed does not wet or drip, and it ensures cooling through a dry contact with the skin of the wearer, leading to great comfort for him.

As a further advantage of the invention it can be noticed that the particles in their initial dry powder state are of low hindrance. The increase in volume takes place on contact with water, when the particles swell into a gel mass. After swelling, the gel formed remains homogeneous and provides the coolness effect for several days. There does not occur any denaturation or variation in the product when it is warmed to temperatures not exceeding 100° C.

Example 1

Several tests have been carried out with an article according to the invention conformed as a headband, obtained by incorporating particles of a superabsorbent sodium polyacrylate medium wherein the individual polymer particles had been subjected to an additional surface selective crosslinking, into a stitched woven textile envelope. The particles were as obtained by the process of European Patent Application EP 0,789,048 and conformed to the following properties: —their saline water absorptivity equals at least 50 g/g; —a bed of the gel of 1.5 g of the polymer under a load of 5 kPa has a saline water absorption of at least 20 g/g.

The initial size of the polymer particles used, measured when dry in the dehydrated state, i.e. before immersion in water, is between 30 and 1500 µm, and preferably between 100 and 800 µm. Preferably, less than 1% of the particles are smaller than 100 µm.

The textile envelope is made of a polyester-cotton woven fabric, which has not be treated with dye fixers. It is composed of two different parts with two identical longitudinal tubular front bags receiving the polymer particles, which are intended to be applied on the forehead, and an elastic band, sewn to the front bags, that, when the headband is worn around the head, is situated at the back of the head and maintains said front bags in close contact with the forehead. The length of the bags is from 25 to 30 cm (28.5 cm in the example), so that they cover the forehead in its entire length. Their thickness or diameter when fully swollen is about 1.5 to 2 cm. The following experiment was carried out:

The headband is immersed in water for one or two minutes, to allow the particles to swell into a gel mass. The gel then occupies homogeneously the entire volume of both bags. The headband is then optionally stored in a freezer for 30 minutes.

When applying it on the head, the feeling of coolness is immediate, due to the thermal shock between the cold envelope and the forehead. The contact is furthermore very tight and homogeneous on the entire forehead, due to the elastic band and to the flexibility of the front part of the headband, confered to it by the form of its two round elongated bags.

The cooling effect remains for a long period. Indeed, three days after wetting, upon applying the headband on the forehead, the feeling of coolness is still immediate. The volume of the front part has started decreasing and the envelope is dry. After four days, the envelope has lost part of its tension, but the bags are still well-shaped. After five days, the thickness of the front part has reduced to almost the same as that of the elastic part. The particules are though still uniformely dispatched in the bags.

In this experiment, where the headband was always kept in room condition of temperature and humidity and was only worn from times to times, it was not before five or six days after wetting and cooling that, when applying the article on the forehead, the user would no longer feel it as ice immediately. However, even then, after having worn it for a few minutes, the impression of coolness would be recovered, which could not be explained but as being due to the evaporation of water from the polymer particles. At that stage, the particles have not yet come back to hard granules. They are still individually in the gel form, but they are separate, not completely swollen, and they concentrate into a small volume at an end of the bags.

Similar articles may be produced for other uses in medecine, such as:
- as an anti-inflammatory agent in the treatment of inflammatory disorders, especially abdominal or dental post-operative disorders, and in the treatment of pain in general;
- in pediatrics, for treating hyperthermia in infants;
- for traumatic postoperative treatments and for general traumatology;
- for example, in the form of cooling stockings or socks in the treatment of venous deficiencies and blood-circulation pathologies;
- for treating rheumatic pathologies, for example abarticular rheumatic pathologies of tendinous origin, or for traumatic post-operative treatments and for general traumatology;
- for the manufacture of a medical compress, which optionally may contain one or more therapeutic agents.

Example 2

Another beneficial application of articles according to the invention is that of heat protection for people working at high temperatures, especially in the metal-conversion industry, in the steelmaking industry, or for firemen.

Jackets produced according to the invention, for example 35 cm by 40 cm, worn over a person's torso, increase the time this person can support exposure to high temperatures by a factor of at least six.

In order to demonstrate the aforementioned long-lasting cooling effect, a measurement experiment was performed on a man, according to the following protocol;
Shape and size of the article : a 13 cm×27 cm patch filled over 10 cm×10 cm with particles of superabsorbent crosslinked sodium acrylate as described in European Patent Application EP-A-0,789,048.
Temperature in the room: 18° C.
Temperature of the absorbed water: 10° C.
The change in temperature over time is indicated below:

| Duration | Temperature of the article |
|---|---|
| Time 0 | 11.8° C. |
| Time 5 min. | 12.5° C. |
| Time 10 min. | 12.9° C. |
| Time 15 min. | 13.6° C. |
| Time 20 min. | 14.3° C. |
| Time 25 min. | 14.7° C. |
| Time 30 min. | 15.5° C. |

Thus, it is found that the temperature of the article increases only by 3.7° C. in thirty minutes, this increase being, moreover, almost linear, which is not the general case with known cooling articles, these instead following a quasi-exponential curve over the same period of time.

Example 3

In the examples above, a woven cotton fabric was used so as to avoid the drawbacks or non-woven fabrics available, such as imperviousness, low resistance to the pressure exerted by the swollen gel, tendency to split, heat insulating properties. However, making the envelope from non-woven fabrics has the advantage that their manufacturing cost is lower than that of woven ones. Thence, a suitable non-woven fabric has been developed that is non-watertight and does not split, that shows high pressure resistance and thermal conductivity and can stand many absorption/desorption cycles.

The fabric used to make the bag's envelope in the preferred embodiments of the invention is a non-woven fabric made of longer threads or fibers of natural or semi-synthetic nature, preferably of a cellulosic material, and more specially threads or fibers of viscose, and shorter polyester fibers, preferably polyethylene fibers and more specially polypropylene fibers. The respective proportions expressed as weight percentages are from 70 to 90 percent for the latter and 10 to 30 percent for the former in the total weight of the composition.

In a specific embodiment, the non-woven fabric comprises 85% polypropylene and 15% viscose rayon under a thickness of 0.6 millimeters and a surface weight of 48 g/m$^2$. That fabric is stable at the hydrophobic/hydrophilous equilibrium point and it can stand more than twenty wettings without loosing its properties. Its strength in resisting to breaking is more than 50 N in the manufacturing or fibers length direction and still higher than 12 N in the cross direction, both whether the fabric is dry or wet. Its absorption capacity is above 600 percent.

Furthermore, the amount of superabsorbent particles placed in the envelope is in excess compared to that required to occupy the whole volume when they are in the full swollen state. Preferably the operation of the article of the invention involves that the polymer particles medium thus in excess in the bag is swollen with absorbed water by immersion in water at a cool temperature (for instance at approximately 10° C. as mentioned above), and when the absorption is blocked, mainly due to the restricted volume in the envelope, but possibly also because of the immersion being performed in cool water or in addition by optionally taking the article out of the cool water bath before that stage, the swollen gel remains able to absorb more water.

Due to their shell-core structure, the particles are distributed while swelling in the entire bag volume, and the less swollen ones, which retain the higher water absorption capacity, are expelled to the periphery of the bag. The amount of particles Introduced in the envelope is thus calculated so that the particles close to the envelope retain a high absorption rate, at least over 70%, thence they are still able to absorb water, moisture, sweat . . . As a consequence, in connection with its inherent water-repellent properties, the envelope remains dry during all the time of application of the article on the user's sore part. On the contrary, too high an excess of particles would lead to such a decrease of the volume in the envelope available for absorption of water, that it would result in loss of part of the cooling capacity of the article. The excess amount of absorbent particles is thence be calculated so as to achieve the best residual absorption rate of the partly unswollen particles after immersion in water, without interfering significantly with the strong and long-lasting cooling effect of the article.

In the preferred embodiments the weight excess of particles is between 5 and 10 percent of the theoretical weight required to just fill the bag completely. It is for instance equal to 8 percent of that amount. After immersion in water is completed, the initial absorption rate is then approximately 80%, and more generally from 70 to 90%, at least for the polymer particles nearer to the bag surface, the particles next to the envelope being less swollen than those in depth.

If immersion in water of the article is long enough, the swelling of the particles is blocked due to the lack of space inside the bag. The material for the envelope must thence support the pressure exerted by the incompletely swollen gel. That problem is solved according to the invention as described above.

Example 4

In order to illustrate the high thermal properties of headbands constituted with articles according to the invention compared to the prior art, the following temperature uptake experiment was carried out.

The headband according to the invention, as constituted according to example 1, is designed here by SM, the one according to example 3 is designed as NM, and a headband containing a gel of absorbent polymer particles wherein there is no substantial difference in the cross-linking rate between core and shell as described by the prior art is called BG.

All three samples are wetted then cooled down to 0° C. The SM sample reaches 0° C. three hours before the BG sample. The temperature uptake of the samples is then monitored during 120 min., The results are shown in the following table, indicating the heat uptake values in ° C.

| Time (min.) | SM (° C.) | NM (° C.) | BG (° C.) |
| --- | --- | --- | --- |
| 0 | 0 | 0 | 0 |
| 3 | 0 | 1.4 | 4 |
| 10 | 0 | 2.8 | 8 |
| 20 | 0.5 | 4.2 | 11.5 |
| 30 | 3.5 | 6.48 | 15 |
| 40 | 4.5 | 9.28 | 16 |
| 50 | 8.5 | 11 | 18 |
| 60 | 11.5 | 13.4 | 19 |
| 120 | 18 | 20.5 | 23.5 |

As shown by these results, the headbands according to the invention show a lower temperature uptake than the headband of the prior art. The uptake difference is particularly high during the first 40 min. of the experiment. Furthermore, the temperature uptake of the SM sample only begins after 20 min, whereas the BG sample already increases its temperature of 11.5° C. during this period.

Indeed the heat uptake in the BG sample increases following an exponential curve starting with a steep slope, whereas the uptake progresses very slowly in the case of the SM sample. With the NM sample, the temperature increase is also very slow compared to the BG sample, and compared to the SM sample, it shows the advantage that the heat uptake follows a linear curve over the time of the experiment.

We claim:

1. An article with cooling capability by water desorption from a water-swollen gel, comprising:
   a polymer absorbent enclosed within a bag delimited by a collapsible envelope having non-watertight walls,
   wherein said polymer absorbent is in particulate form wherein each particle comprises a core of less cross-linked polymer sequences for retaining absorbed water and a shell of more cross-linked polymer sequences for retarding diffusion of water from a particle to another during desorption of absorbed water, and
   wherein the amount of polymer particles enclosed in the bag is in excess compared to the theoretical amount that would be just required to fill up the bag when they are in the full swollen state.

2. An article according to claim 1, wherein said polymer has a sodium polyacrylate base.

3. An article according to claim 1, wherein said envelope is made of a cotton woven textile fabric.

4. An article according to claim 1, wherein said envelope is made of a cotton-viscose woven textile fabric.

5. An article according to claim 1, wherein said envelope is made of a non-woven fabric of viscose and polyester fibers.

6. An article according to claim 1, wherein said excess is from 5 to 10 percent by weight of the theoretical amount required to just fill the bag completely.

7. An article according to claim 1, wherein said envelope is made of a non-woven fabric comprising longer threads or fibers of natural or semi-synthetic nature and shorter polyester fibers, the respective proportions expressed as weight percentages being from 70 to 90 percent for the latter and from 10 to 30 percent for the former in the total weight of the composition.

8. An article according to claim 7, wherein said longer threads or fibers are made of a cellulosic material.

9. An article according to claim 7, wherein said longer threads or fibers are viscose fibers.

10. An article according to claim 7, wherein said shorter fibers are polypropylene fibers.

11. An article according to claim 1, wherein said envelope is made of a non-woven fabric comprising longer threads or fibers of viscose and shorter polypropylene fibers, the respective proportions expressed as weight percentages being from 70 to 90 percent for the latter and from 10 to 30 percent for the former in the total weight of the non woven fabric.

12. A method for relieving pain from a sore part of an individual's body with a cooling article comprising a polymer absorbent enclosed within a bag delimited by a collapsible envelope having non-watertight walls, wherein said polymer absorbent is in particulate form wherein each particle comprises a core of less cross-linked polymer sequences for retaining absorbed water and a shell of more cross-linked polymer sequences for retarding diffusion of water from a particle to another during desorption of absorbed water, said method comprising:
   wetting said polymer particles with water through said envelope during a sufficient time to swell them into a gel mass filling up said bag, and
   applying said article on said sore part of the individual's body maintaining an inner wall in close contact thereon while allowing water vapor desorbed from said particles to escape through an opposed outer wall of said envelope.

13. An article with cooling capability by water desorption from a water-swollen gel, comprising:
a polymer absorbent enclosed within a bag delimited by a collapsible envelope having non-watertight walls and made of a non-woven fabric comprising longer threads or fibers of natural or semi-synthetic nature and shorter polyester fibers,
wherein said polymer absorbent is in particulate form wherein each particle comprises a core of less cross-linked polymer sequences for retaining absorbed water and a shell of more cross-linked polymer sequences for retarding diffusion of water from a particle to another during desorption of absorbed water, and wherein said polymer absorbent has a sodium polyacrylate base, and
wherein the amount of polymer particles enclosed in the bag is in excess compared to the theoretical amount that would be just required to fill up the bag when they are in the full swollen state.

14. An article according to claim 13, wherein said longer threads or fibers are made of a cellulosic material.

15. An article according to claim 13, wherein said longer threads or fibers are viscose fibers.

16. An article according to claim 13, wherein said shorter fibers are polypropylene fibers.

17. An article according to claim 13, wherein said envelope is made of a non-woven fabric comprising longer threads or fibers of viscose and shorter polypropylene fibers, the respective proportions expressed as weight percentages being from 70 to 90 percent for the latter and from 10 to 30 percent for the former in the total weight of the non-woven fabric.

18. An article according to claim 13, wherein said excess is from 5 to 10 percent by weight of the theoretical amount required to just fill the bag completely.

19. An article according to claim 1, wherein the article relieves pain from a sore part of an individual's body by a cooling effect.

20. An article according to claim 13, wherein the article relieves pain from a sore part of an individual's body by a cooling effect.

21. A method according to claim 12, wherein the amount of polymer particles enclosed in the bag is in excess compared to the theoretical amount that would be just required to fill up the bag when they are in the full swollen state.

22. A method according to claim 21, wherein during said applying, non-fully swollen particles of said polymer absorbent are disposed close to the walls of the bag to absorb traces of moisture penetrating into the bag through the envelope.

23. A method according to claim 12, wherein said sore part of the individual's body is normally dry.

* * * * *